(12) United States Patent
Pacetti et al.

(10) Patent No.: US 7,507,211 B2
(45) Date of Patent: *Mar. 24, 2009

(54) GUIDE WIRE AND METHOD OF MAKING SAME

(75) Inventors: Stephen D. Pacetti, San Jose, CA (US); Douglas H. Gesswein, Temecula, CA (US); Emmanuel C. Biagtan, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 285 days.

This patent is subject to a terminal disclaimer.

(21) Appl. No.: 10/990,654

(22) Filed: Nov. 17, 2004

(65) Prior Publication Data

US 2005/0070793 A1    Mar. 31, 2005

Related U.S. Application Data

(63) Continuation of application No. 10/335,783, filed on Jan. 2, 2003, now Pat. No. 6,845,259, which is a continuation of application No. 10/034,715, filed on Dec. 26, 2001, now Pat. No. 6,799,067.

(51) Int. Cl.
    *A61M 25/00* (2006.01)
(52) U.S. Cl. ........................ 600/585; 29/428
(58) Field of Classification Search ......... 600/407–472, 600/585, 657, 658; 604/280–282; 606/108; 29/592, 897, 428, 525.01, 527.01
    See application file for complete search history.

(56) References Cited

U.S. PATENT DOCUMENTS

| | | | |
|---|---|---|---|
| 2,857,915 A | 10/1958 | Sheridan | |
| 3,485,234 A | 12/1969 | Stevens | |
| 3,529,633 A | 9/1970 | Vaillancourt | |
| 3,585,707 A | 6/1971 | Stevens | |
| 3,608,555 A | 9/1971 | Greyson | |
| 3,994,607 A * | 11/1976 | Kikuchi et al. | 403/284 |
| 4,966,163 A * | 10/1990 | Kraus et al. | 600/585 |
| 4,989,608 A | 2/1991 | Ratner | |
| 5,061,395 A | 10/1991 | Meng | |
| 5,154,179 A | 10/1992 | Ratner | |
| 5,409,015 A | 4/1995 | Palermo | |
| 5,439,000 A | 8/1995 | Gunderson et al. | |
| 5,479,938 A | 1/1996 | Weier | |

(Continued)

OTHER PUBLICATIONS

John F. Schenck, The role of magnetic susceptibility in magnetic resonance imaging: MRI magnetic compatability of the first and second kinds, Med Phys. 23 (6), 816 850 (1996).

(Continued)

*Primary Examiner*—Ruth S Smith
(74) *Attorney, Agent, or Firm*—Fulwider Patton LLP

(57) ABSTRACT

An improved intracorporeal device such as a guide wire or other guiding member for use within a patient's body that is at least in part visible under magnetic resonance imaging (MRI) but is not detrimentally affected by the imaging is disclosed. The intracorporeal device has a non-conductive proximal core section, an essentially non-magnetic metallic distal core section that is preferably more flexible than the proximal core section, and that has an MRI visible member or coil in the distal section.

14 Claims, 1 Drawing Sheet

U.S. PATENT DOCUMENTS

| | | | |
|---|---|---|---|
| 5,487,739 A | | 1/1996 | Aebischer et al. |
| 5,516,336 A | | 5/1996 | McInnes et al. |
| 5,573,508 A | * | 11/1996 | Thornton ............... 604/102.02 |
| 5,601,087 A | | 2/1997 | Gunderson et al. |
| 5,637,089 A | | 6/1997 | Abrams et al. |
| 5,769,796 A | | 6/1998 | Palermo et al. |
| 5,792,055 A | | 8/1998 | McKinnon |
| 5,824,055 A | | 10/1998 | Spiridigliozzi et al. |
| 5,848,964 A | | 12/1998 | Samuels |
| 5,897,536 A | | 4/1999 | Nap et al. |
| 5,947,995 A | | 9/1999 | Samuels |
| 5,951,480 A | | 9/1999 | White et al. |
| 5,951,494 A | | 9/1999 | Wang et al. |
| 5,961,511 A | * | 10/1999 | Mortier et al. ............... 604/527 |
| 6,001,068 A | * | 12/1999 | Uchino et al. ............... 600/585 |
| 6,014,580 A | | 1/2000 | Blume et al. |
| 6,019,737 A | | 2/2000 | Murata |
| 6,026,316 A | | 2/2000 | Kucharczyk et al. |
| 6,061,587 A | | 5/2000 | Kucharczyk et al. |
| 6,095,990 A | | 8/2000 | Parodi |
| 6,106,473 A | | 8/2000 | Violante et al. |
| 6,165,139 A | | 12/2000 | Damadian |
| 6,165,292 A | | 12/2000 | Abrams et al. |
| 6,171,240 B1 | | 1/2001 | Young et al. |
| 6,171,250 B1 | | 1/2001 | White et al. |
| 6,190,353 B1 | | 2/2001 | Makower et al. |
| 6,203,568 B1 | | 3/2001 | Lombardi et al. |
| 6,241,703 B1 | * | 6/2001 | Levin et al. .................... 604/22 |
| 6,241,744 B1 | | 6/2001 | Imran et al. |
| 6,248,076 B1 | | 6/2001 | White et al. |
| 6,261,246 B1 | | 7/2001 | Pantages et al. |
| 6,261,247 B1 | | 7/2001 | Ishikawa et al. |
| 6,272,370 B1 | | 8/2001 | Gillies et al. |
| 6,280,539 B1 | | 8/2001 | Abrams et al. |
| 6,402,706 B2 | * | 6/2002 | Richardson et al. ......... 600/585 |
| 6,702,762 B2 | | 3/2004 | Jarari et al. |
| 6,799,067 B2 | * | 9/2004 | Pacetti et al. ................. 600/431 |
| 6,845,259 B2 | * | 1/2005 | Pacetti et al. ................. 600/407 |
| 6,893,456 B2 | * | 5/2005 | Lumauig ................... 623/1.11 |
| 6,918,882 B2 | * | 7/2005 | Skujins et al. ............... 600/585 |
| 2004/0102720 A1 | | 5/2004 | Kellerman et al. |

OTHER PUBLICATIONS

Lee P. Bendel et al., The Effect of Mechanical Deformation on Magnetic Properties and MRI Artifacts of Type 304 and Tupe 316L Stainless Steel, JMRI, vol. 7, No. 6 1170 1173 (1997).

Chris J. Bakker et al., *MR-Guided Balloon Angioplasty: In Vitro Demonstration of the Potential of MRI for Guiding, Monitoring, and Evaluating Endovascular Interventions*, JMRI, vol. 8, No. 1, 245-250 (1998).

Paul R. Hilfiker et al., *Plain and Covered Stent-Grafts: In Vitro Evaluation of Characteristics at Three-dimensional MR Angiography*, Radiology, vol. 211, No. 3 693-697 (1999).

Maurits K. Kongings et al., *Heating Around Intravascular Guidewires by Resonating RF Waves*, JMRI, vol. 12, No. 1, 79-85 (2000).

L.W. Bartels et al., *MR-guided Balloon Angioplasty of Stenosed Hemodialysis Access Grafts*, Proc. Intl. Soc. Mag. Reson. Med. 8, 409 (2000).

C. Manke et al., Stent Angioplasy of Iliac Artery Stenoses under MR-control: Initial Clinical Results, Fortschr Rontgenstr; 172: 92-97 (2000).

Chia-Ying Liu et al., Safety of MRI-Guided Endovascular Guidewire applications, JMRI 12:75-78 (2000).

Wolfgang R. Nitz et al., On the Heating of Linear Conductive Structures as Guide Wires and Catheters in Intervnentional MRI, JMRI 13:105-114 (2001).

* cited by examiner

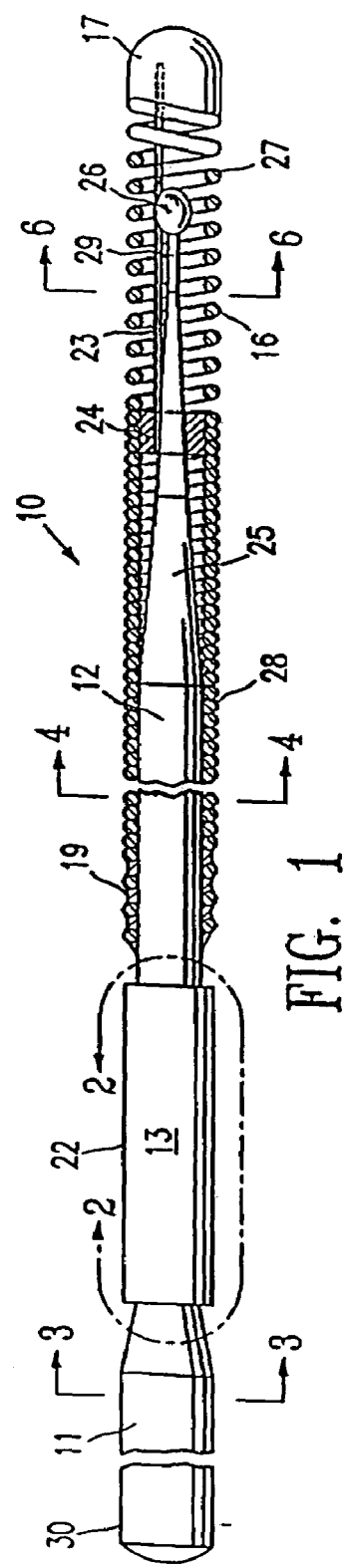

GUIDE WIRE AND METHOD OF MAKING SAME

CROSS-REFERENCES TO RELATED APPLICATIONS

This is a continuation of application Ser. No. 10/335,783, filed Jan. 2, 2003, now U.S. Pat. No. 6,845,259,which is a continuation of application Ser. No. 10/034,715, filed Dec. 26, 2001, now U.S. Pat. No. 6,799,067, all of whose contents are hereby incorporated by reference.

FIELD OF THE INVENTION

This invention relates generally to the field of medical devices, and more particularly to a guide wire for advancing a catheter or other intraluminal device within a body lumen in a procedure such as percutaneous transluminal coronary angioplasty (PTCA) or stent delivery which is observed by Magnetic Resonance Imaging (MRI).

BACKGROUND OF THE INVENTION

Conventional guide wires for angioplasty and other vascular procedures usually comprise an elongated core member with one or more tapered sections near the distal end thereof and a flexible body such as a helical coil disposed about the distal portion of the core member. A shapeable member, which may be the distal extremity of the core member or a separate shaping ribbon which is secured to the distal extremity of the core member, extends through the flexible body and is secured to a rounded plug at the distal end of the flexible body. Torquing means are provided on the proximal end of the core member to rotate, and thereby steer, the guide wire while it is being advanced through a patient's vascular system.

In a typical PTCA procedure, a guiding catheter having a preformed distal tip is percutaneously introduced into the cardiovascular system of a patient in a conventional Seldinger technique and advanced therein until the distal tip of the guiding catheter is seated in the ostium of a desired coronary artery. A guide wire is positioned within an inner lumen of a dilatation catheter and then both are advanced through the guiding catheter to the distal end thereof. The guide wire is first advanced out of the distal end of the guiding catheter into the patient's coronary vasculature until the distal end of the guide wire crosses a lesion to be dilated, then the dilatation catheter having an inflatable balloon on the distal portion thereof is advanced into the patient's coronary anatomy over the previously introduced guide wire until the balloon of the dilatation catheter is properly positioned across the lesion. Once in position across the lesion, the balloon is inflated to a predetermined size with radiopaque liquid at relatively high pressures (e.g., greater than 4 atmospheres) to press the arteriosclerotic plaque of the lesion against the inside of the artery wall and to otherwise expand the inner lumen of the artery. The balloon is then deflated so that blood flow is resumed through the dilated artery and the dilatation catheter can be removed therefrom.

A major requirement for guide wires is that they have sufficient column strength to be pushed through a patient's vascular system or other body lumen without kinking. However, they must also be flexible enough to avoid damaging the blood vessel or other body lumen through which they are advanced. Efforts have been made to improve both the strength and flexibility of guide wires to make them more suitable for their intended uses, but these two properties are for the most part diametrically opposed to one another in that an increase in one usually involves a decrease in the other.

Currently, x-ray fluoroscopy is the preferred imaging modality for cardiovascular interventional procedures because no other imaging method has the temporal or spatial resolution provided by fluoroscopy. However, x-ray imaging has many drawbacks for both the patient and the clinician. The iodinated contrast agents employed in x-ray fluoroscopy are nephrotoxic with a low but measurable incidence of short-term renal failure and allergic reactivity. The ionizing radiation from the x-ray fluoroscopy can be an issue for the patient during protracted or repeated interventions and is a daily issue for the interventionalist and staff who must cope with the burden of personal dose monitoring and wearing lead shielding.

The use of MRI for observing interventional procedures has been performed for balloon angioplasty and stent placement. The use of this imaging modality is quite attractive because it eliminates some of the problems inherent with x-ray imaging. On the other hand, conventional guide wires which are suitable for x-ray fluoroscopy are not suitable for use in MRI observed interventional procedures due to their magnetic attraction, large magnetic susceptibility artifact, and potential heating when exposed to RF energy.

What has been needed and heretofore unavailable is a guide wire which is safe and compatible for use in conjunction with MRI. The present invention satisfies these and other needs.

SUMMARY OF THE INVENTION

The present invention is directed to an intracorporeal device such as a guide wire which is safe, compatible and readily visible with MRI. An intracorporeal device embodying features of the invention preferably has an elongated member with an electrically non-conductive proximal section, an essentially non-magnetic distal core section, and a metallic coil disposed about and secured to the distal core section with a small magnetic susceptibility to act as an MRI visible marker. That is, the coil or a marker thereon has a magnetic susceptibility that facilitates the observation thereof within the patient under MRI.

The distal end of the proximal non-conductive core section and the proximal end of the non-magnetic but conductive distal core section can be secured together by any non-conductive means including polymeric or metallic sleeves so long as the joint between these members results in a torque transmitting relationship therebetween.

The selection of materials for component parts of the intracorporeal device, such as a guide wire, including the proximal section, the distal section and the MRI visible member secured to the distal section are based upon the mechanical and physical properties needed for the intended use. The materials from which the MRI compatible device is made need to overcome three basic factors: magnetic attraction of magnetic members, RF heating effects of conductive members, and visualization under MRI.

Forming the proximal section from non-conductive, non-metallic material and the distal section and MRI visible member from non-magnetic materials resolves the magnetic attraction of these members during MRI. The non-conductive, non-metallic nature of the proximal core section and the length of the distal core section alone or in conjunction with the MRI visible member resolve the RF heating of these members. Controlling the level of magnetic susceptibility of the material from which the MRI visible member is formed resolves the visualization issue.

Suitable materials for the non-conductive proximal section of the intracorporeal device include optical fibers (single or a bundle of fibers), fiberglass, carbon fiber-epoxy composites, composites of oriented polyethylene fiber (e.g., Spectra®), composites of polyaramide fiber (e.g., Kelvar®) and composites of these materials with engineering resins such as polysulfone, polyethersulfone, polyetherimide, vinylester, cyanate ester, phenolic, polyurethane, polyimide and polyetheretherketone. The MRI visible member or marker and preferably also the distal section are formed of suitable non-magnetic materials that may be electrically conductive. Suitable materials include one or more metallic materials selected from the group consisting of platinum, nitinol, niobium, titanium, tantalum, zirconium, iridium, aluminum, silver, gold, indium, and alloys thereof.

The distal core section and the tip coil are formed of suitable non-magnetic conductive materials having the correct amount of magnetic susceptibility artifact for accurate imaging. The volumetric magnetic susceptibility suitable for visualization under MRI for these structures is less than or equal to about $280 \times 10^{-6}$ (SI), and preferably less than about $245 \times 10^{-6}$ (SI).

The intracorporeal devices embodying features of the present invention are in part readily visible under MRI and they have desirable characteristics for performing intracorporeal procedures. These and other advantages of the invention will become more apparent from the following detailed description thereof when taken in conjunction with the following exemplary drawings.

BRIEF DESCRIPTION OF THE DRAWINGS

FIG. 1 is a side elevational view, partially in section, of a guide wire that embodies features of the present invention.

FIG. 2 is an enlarged, side elevational view, partially in section, of the junction between the proximal and distal core sections of the guide wire shown in FIG. 1 taken within line 2-2.

FIG. 3 is a cross-sectional view of the guide wire shown in FIG. 1 taken along the line 3-3.

FIG. 4 is a cross-sectional view of the guide wire shown in FIG. 1 taken along line 4-4.

FIG. 5 is a cross-sectional view of the guide wire connection shown in FIG. 2 taken along the line 5-5.

FIG. 6 is a cross-sectional view of the guide wire shown in FIG. 1 taken along line 6-6.

FIG. 7 is a side elevational view, partially in section, of an alternative distal core section having non-conductive junctions between conductive core segments.

DETAILED DESCRIPTION OF THE PREFERRED EMBODIMENTS

FIGS. 1-6 illustrate an embodiment of an MRI compatible guide wire 10 embodying features of the present invention that is used in a patient's body lumen, such as an artery or vein. In one aspect, a process for joining two guide wire core materials can involve grinding at least one of the distal end 14 of the proximal core section 11 and the proximal end 15 of the distal core section 12. The guide wire 10 generally comprises an elongated, relatively non-conductive proximal core section 11, a relatively short, non-magnetic, metallic distal core section 12, a polymeric connecting element 13 securing together the distal end 14 of the proximal core section 11 and the proximal end 15 of the distal core section 12. A helically shaped metallic coil 16, formed at least in part of non-magnetic material, is disposed about and secured to the distal core section 12. The coil 16 is secured at its distal end by a rounded body 17 of solder, weldment, or adhesive, at an intermediate location by a mass 24 of solder or adhesive, and at its proximal end by a mass 19 of solder, adhesive or other suitable material that joins the coil 16 to the distal core section 12.

The guide wire 10 shown in FIG. 1 generally has conventional intravascular guide wire features and the particular embodiment shown is commonly called a "floppy" guide wire due to the shaping ribbon 23 which extends from the distal core section 12 to the rounded mass 17. The distal end of the shaping ribbon 23 is secured to the end of the coil 16 by the mass 17 and the proximal end thereof is secured by intermediate mass 24 of connecting material which also secures an intermediate portion of the coil 16 to the distal core section 12. The distal core section 12 optionally has at least one tapered section 25 with smaller transverse dimensions in the distal direction. The rounded distal tip 26 of the distal core section 12 is so configured to prevent the end of the distal core section from extending through the spacing between the turns of the coil 16 when the guide wire 10 passes through tortuous anatomy.

The polymeric connecting element 13, which is shown in detail in FIG. 2, is a polymeric member that is disposed about and secured to the undulated distal end 20 of the proximal core section 11 and the undulated proximal end 21 of the distal core section 12. This embodiment of the connector element 13 generally has a cylindrical exterior 22 that has an outer diameter about the same as the outer diameter of the coil 16 and the outer diameter of the proximal core section 11. The ends 20 and 21 of the proximal core section 11 and the distal core section 12 may be given an undulated shape as shown in FIG. 2 to provide a mechanical interlock or friction fit with the polymeric material of the connecting element 13 which is secured about the ends 20, 21.

The connection between the ends 20 and 21 of the proximal and distal core sections 11 and 12, respectively, may be made by positioning the distal end 20 of the proximal core section 11 and the proximal end 21 of the distal core section 12 in close proximity to each other within the interior of a mold which preferably has a cylindrical interior molding surface of the desired dimensions of the exterior surface 22 of the connecting member 13. Polymerizable or otherwise hardenable non-conductive material is introduced into the interior of the mold and polymerized or otherwise hardened into a polymeric or other non-metallic mass about the ends 20 and 21 so as to fix the ends within the connecting element 13. The hardenable non-conductive material forming the connection between the proximal and distal core sections 11 and 12 is sufficiently strong to facilitate torque transmission between these core sections.

Suitable non-magnetic, and preferably polymeric materials for the connecting element 13 include one or more thermoplastic polymeric materials such as a polyester, polyetheretherketone, ABS, and epoxy materials or co-polymers or blends thereof. The polymeric materials may be blends of a variety of polymeric materials. The polymeric material is preferably selected so that the connecting element 13 holds the two core sections together to effect torque transmission and to provide a smooth transition between the proximal and distal core sections 11 and 12, respectively. It will be appreciated that, in light of the foregoing, and of the fact that the connector element 13 of this embodiment has a cylindrical exterior 22 that has an outer diameter about the same as the outer diameter of the proximal core section 11, and further as exemplified in FIG. 2, the connecting element 13 of this embodiment is not covered by a hypotube.

The proximal section 11 of one embodiment of the guide wire 10 is fabricated from metals such as work hardened 304V stainless steel. In order to have similar tracking, torque, and push properties, proximal sections of polymeric and composite materials would ideally have similar properties. One important property to match is stiffness both laterally and axially while hardness is of lesser importance. To achieve the preferred properties of a guide wire, any proximal shaft of a polymeric material would be a composite. Further, the polymer component may be a thermoset or a thermoplastic. Exemplary of common thermosets include epoxy, polyester, vinylester, cyanate ester, phenolic, polyurethane, and polyimide. Suitable fiber reinforcement materials include fiberglass, s-glass, e-glass, graphite, Kevlar®, Twaron®, Nomex®, Spectra®, polyaramid, carbon, boron, and boron nitride.

Fiberglass components may also be used in fabricating the guide wire, recognizing that fiberglass is typically a composite of a polyester resin with a glass fiber reinforcement. Guide wires fabricated entirely from fiberglass, however, do not have the functional advantages of a distal metallic section 12 and metallic tip coil 17.

Composite guide wire structures of fiber reinforced polymeric materials may be made by methods of extrusion, pultrusion, injection molding, transfer molding, flow encapsulation, fiber winding on a mandrel, or lay up with vacuum bagging. Epoxy resins are available from a variety of manufacturers including Ciba Specialty Chemicals, Shell Chemical, Dow Chemical, and Gougeon Brothers, Inc. Sources of carbon fiber include Hexcel Corp., Amoco, Toho, Rayon, and Toray. Exemplary of non-composite materials for the non-conductive proximal section 11 include glass fiber optics (available from Corning Glass and Seiko Instruments, Inc.) and ceramics.

The examples set forth in detail below illustrate the fabrication of a composite proximal shaft of a guide wire in accordance with the present invention. In the first exemplary embodiment, a composite proximal shaft is fabricated with IM7 carbon fibers (available from Hexcel Corp.) and an Epon epoxy resin system (available from Shell Corp.). Using pultrusion, a shaft of 67 volume percent carbon fiber is fabricated. A 20 cm distal section of nitinol is affixed to the shaft using a sleeve joint. A tip coil of 90/10 tantalum/tungsten alloy is attached by soldering to the distal end of the nitinol section.

In the second exemplary embodiment, a composite proximal shaft is fabricated of Victrex™ PEEK 450CA30 (30% carbon reinforced) by extrusion. Optional bands of palladium are attached to the shaft at 10 cm intervals to function as passive paramagnetic susceptibility markers. The 20 cm distal metallic shaft is fabricated of CP (commercially pure) titanium (Wah Chang). A 90/10 platinum/iridium tip coil is attached via soldering to the titanium section.

As seen in FIG. 1, one embodiment of a guide wire 10 having features of the present invention generally includes an elongated core member with an electrically non-conductive proximal core section 11, a metallic distal core section 12 with low magnetic susceptibility, and a metallic tip coil 27 extending from the distal end of the distal core section 12.

The non-electrically conductive proximal core section 11 is MRI safe with regard to both attractive forces and RF heating effects. This distal core section 12 between the non-conductive proximal core section 11 and the tip coil 27 is analogous to the distal nitinol section of a conventional guide wire. Its maximum safe length can be estimated from the magnetic field strength of the MRI scanner. At 1.5 T, antenna theory predicts that a guide wire can behave as a dipole antenna beginning at a length of 23 inches (about 58 cm).

Preferably, the metallic tip coil 27 and the distal core section 12 (the conductive members) are connected with a non-conductive insulator so that they do not act in concert as a single dipole antenna. If the metallic tip coil 27 and the distal core section 12 are separated by a non-conductive material 13, then the length of the distal core section 12 can be up to 23 cm in a magnetic field of 1.5 T. Without the insulator, the 23 cm length applies to the total length of the tip coil 27 and the distal core section 12.

As the RF frequency utilized is linearly proportional to the MRI scanner field strength, lower field strengths of 1.0 T and 0.5 T couple at conductor member lengths of 35 cm and 69 cm, respectively. So at a lower magnetic field strength of 1.5 T, a preferred range for the length of the conductive member is less than 29 cm. A more preferred range of the length of the conductive member is less than 23 cm. The minimum practical length of the conductive section is determined by the length of a functional guide wire tip coil which is approximately 3 cm. These maximum safe lengths are inversely proportional to the magnetic field strength.

The highest field strength MRI scanners in routine clinical use at the present time operate at 3 T. At this strength, a preferred conductor length is less than approximately 14.4 cm, and a more preferred conductor length is less than approximately 11.5 cm. Thus, as the MRI scanner field strength increases, the safe length of the conductive members decreases.

Accordingly, the conductive member in one embodiment has a length of about $L<43.5/B_0$, where "L" represents the electrically conductive length in centimeters, and "$B_0$" represents the scanner magnetic field in Tesla. In a more preferred embodiment, the conductive member has a length of about $L<34.5/B_0$. The experimental and theoretical foundation for these values may be found in the work of Liu et al., *Journal of Magnetic Resonance Imaging*, Vol. 12, pp. 75-78 (2000), and Nitz et al., *Journal of Magnetic Resonance Imaging*, Vol. 13, pp. 105-114 (2001), the contents of which are incorporated herein by reference.

FIG. 7 illustrates another embodiment in which the length of the metallic distal core section (conductive member) is limited. In particular, the distal core section 12 may be formed in multiple metallic segments 31 and 32 separated by a non-conductive joint 33. This construction provides a longer metallic distal core section with each of the metallic segments being kept short enough so as to not be heated when subjected to the magnetic fields generated by the MRI to provide greater length distal sections.

The electrical conductivity of the non-conductive proximal core section 11 is electrical resistivity expressed in micro-ohm-cm. The higher the value for electrical resistivity, the more resistance for the material of the proximal core section. Based on research using nitinol guide wires, for example, it has been found that at about 100 micro-ohm-cm, a nitinol guide wire is conductive enough to heat in an MRI scanner. However, little research has been done examining how conductive a long wire can be in an MRI and still avoid heating. Models of this effect have considered resistance of the wire to be negligible. The minimum resistivity for the non-conductive proximal core section is estimated to be approximately 0.01 ohm-cm.

The coil 16 may also be formed by two separate coil segments: a distal coil segment 27 which is formed of a non-magnetic material having the requisite magnetic susceptibility to provide MRI visibility, and a proximal coil segment 28 which may be made of another material having other desirable properties such as radiopacity. Additionally, the distal coil segment 27 of the coil 16 may be stretched about 10 to about 30% in length as shown in FIG. 1 to provide increased flexibility.

The elongated proximal core section 11 may be an optical fiber which should be provided with a coating 30 of lubricous material such as a fluoropolymer, polytetrafluoroethylene sold under the trademark Teflon® by Du Pont de Nemours & Co. Other suitable lubricous coatings include fluoropolymers, hydrophilic coatings and polysiloxane coatings.

The overall length of the guide wire 10 will vary depending upon the procedure and the MRI compatibility parameters mentioned above, but for percutaneous intravascular procedures the guide wire is generally about 100 to about 200 cm in length. Most commercially available guide wires for adult coronary use come in lengths of 175 cm and 195 cm. The outer diameter of the guide wire ranges from about 0.006 to 0.018 inch (0.15-0.45 mm) for coronary use. Larger diameter guide wires, e.g. up to 0.035 inch (0.89 mm) or more may be employed in peripheral arteries and other body lumens. The length of the distal core section can range from about 1 to about 30 cm, depending upon the flexibility and other properties including MRI imaging characteristics desired in the final product. The helical coil 16 may be about 3 to about 45 cm in length, preferably about 5 to about 30 cm and may have an outer diameter about the same size as the outer diameter of the elongated proximal core section 11. The helical coil 16 is preferably made from wire about 0.001 to about 0.003 inch (0.025-0.08 mm) in diameter, typically about 0.002 inch (0.05 mm). The shaping ribbon 21 and the flattened distal section 29 of distal core section 12 can have generally rectangular shaped transverse cross-sections which usually have dimensions of about 0.0005 to about 0.006 inch (0.013-0.152 mm), and preferably about 0.001 by 0.003 inch (0.025-0.076 mm).

In an embodiment of the present invention, the distal core section 12 is made of a metal or alloy material which has a volumetric magnetic susceptibility of less than about $280 \times 10^{-6}$ (SI), and preferably less than about $245 \times 10^{-6}$ (SI). Metals that meet this criteria and their respective volumetric magnetic susceptibility are set forth in the following table. While the distal core section 12 needs to be essentially non-magnetic, it does not necessarily require the volumetric magnetic susceptibility set forth above which provides visibility under MRI.

| MATERIAL | VOLUMETRIC MAGNETIC SUSCEPTIBILITY ($\times 10^{-6}$ (SI)) |
|---|---|
| Platinum | 279 |
| Nitinol | 245 |
| Niobium | 237 |
| Titanium | 182 |
| Tantalum | 178 |
| Zirconium | 109 |
| Iridium | 37.5 |
| Aluminum | 20.7 |
| Silver | −24 |
| Gold | −34 |
| Indium | −51 |

Various polymeric connecting elements 13 embodying features of the invention generally have outer diameters from about 0.006 inch to about 0.02 inch (0.15-0.51 mm), and preferably about 0.10 to about 0.014 inch (2.5-0.356 mm) for coronary guide wires. The overall length of the connecting element 13 may range from about 0.25 to about 3 cm, and typically ranges about 0.75 to about 1.5 cm. Naturally, the connecting elements for guide wires for other medical applications and treatment sites may have dimensions different than that described above.

The proximal core section 11 is formed of a non-conductive material such as an optical fiber (e.g., a single fiber or a bundle of fibers), carbon fiber epoxy composites, composites of oriented polyethylene fiber (e.g., Spectra®), composites of polyaramide fiber (e.g., Kelvar®), and composites of these materials with engineering resins such as polyaryetherketone, polyphenylenesulfide, polyimide and polyetheretherketone. Other suitable non-conductive materials may be used for the proximal core section.

The guide wire embodying features of the invention may be percutaneously introduced into a patient's blood vessel, such as the femoral artery, and advanced within the patient's vasculature under MRI so as to be able to observe the coil at the guide wire distal core section which acts as an MRI visible marker member to ensure that the guide wire or other intracorporeal device is disposed at a desired location within the patient's vasculature. Once the distal portion of the guide wire is in place at the desired location, a therapeutic or diagnostic device may be advanced over the in place guide wire until the operative portion of the intracorporeal device is positioned to perform a therapeutic or diagnostic procedure in a conventional fashion.

While the description of embodiments having features of the invention has been directed primarily herein to guide wires suitable for guiding other devices within a patient's body, those skilled in the art will recognize that these features may also be utilized in other intracorporeal devices such as electrophysiology catheters, pacing leads and the like. References to other modifications and improvements can be made to the invention without departing from the scope of the appended claims.

To the extent not otherwise described herein, the materials and methods of construction and the dimensions of conventional intracorporeal devices such as intravascular guide wires may be employed with a device embodying features of the present invention. Moreover, features disclosed with one embodiment may be employed with other described embodiments. Additionally, reference to the terms "members," "elements," "sections" and terms of similar import in the claims which follow shall not be interpreted to invoke the provisions of 35 U.S.C. § 112 (paragraph 6) unless reference is expressly made to the term "means" followed by an intended function.

We claim:

1. A guide wire, comprising:
   a core having a proximal core section with proximal and distal ends and a distal core section with proximal and distal ends; and a non-conductive joint securing the distal end of the proximal core section to the proximal end of the distal core section;
   wherein the non-conductive joint is not covered by a hypotube and is configured between the distal end of the proximal core section and the proximal end of the distal core section such that the distal end of the proximal core section and the proximal end of the distal core section do not overlie each other, and at least one of the distal end of the proximal core section and the proximal end of the distal core section has an undulated shape.

2. The guide wire of claim 1, wherein the non-conductive joint encases at least one of the distal end of the proximal core section and the proximal end of the distal core section.

3. The guide wire of claim 1, wherein the non-conductive joint includes at least in part one or more thermoplastic polymeric materials selected from the group consisting of polyester, polyetheretherketone, ABS, epoxy, copolymers, and blends thereof.

4. The guide wire of claim 1 wherein the proximal core section is formed exclusively from non-conductive material.

5. The guide wire of claim 1, further comprising a coil configured about the distal core section and connected thereto with a non-conductive insulator.

6. A process for joining two guide wire core materials without using a hypotube, comprising:
providing a proximal core section having a distal end and a distal core section having a proximal end;
grinding at least one of the distal end of the proximal core section and the proximal end of the distal core section;
shaping at least one of the distal end of the proximal core section and the proximal end of the distal core section into an undulating shape; and
at least partially encasing at least one of the distal end of the proximal core section and the proximal end of the distal core section with a non-conductive material such that the non-conductive material is configured between the distal end of the proximal core section and the proximal end of the distal core section so that the distal end of the proximal core section and the proximal end of the distal core section do not overlie each other.

7. The process of claim 6, wherein the non-conductive material includes at least in part of one or more thermoplastic polymeric materials selected from the group consisting of polyester, polyetheretherketone, ABS, epoxy, copolymers, and blends thereof.

8. A guide wire, comprising:
a core having a proximal core section with proximal and distal ends and a distal core section with proximal and distal ends; and
a non-conductive material securing the distal end of the proximal core section to the proximal end of the distal core section;
wherein the non-conductive material is not covered by a hypotube and is configured between the distal end of the proximal core section and the proximal end of the distal core section such that the distal end of the proximal core section and the proximal end of the distal core section do not overlie each other, and at least one of the distal end of the proximal core section and the proximal end of the distal core section has an undulated shape.

9. The guide wire of claim 8, wherein the non-conductive material includes a non-metallic material.

10. The guide wire of claim 8, wherein the proximal core section includes stainless steel.

11. The guide wire of claim 10, wherein the distal core section includes nitinol.

12. The guide wire of claim 8, wherein the non-conductive material includes at least in part one or more thermoplastic polymeric materials selected from the group consisting of polyester, polyetheretherketone, ABS, epoxy, co-polymers, and blends thereof.

13. The guide wire of claim 8, wherein the non-conductive material includes at least one of a polymerizable material and a hardenable non-conductive material.

14. The guide wire of claim 8, further comprising a coil configured about the distal core section and attached thereto by a non-conductive insulator and wherein the proximal core section is made from non-conductive material.

* * * * *